US010485614B2

(12) United States Patent
Jang

(10) Patent No.: US 10,485,614 B2
(45) Date of Patent: Nov. 26, 2019

(54) AUGMENTED REALITY SYSTEM AND METHOD FOR IMPLEMENTING AUGMENTED REALITY FOR DENTAL SURGERY

(71) Applicant: Wonseok Jang, Busan (KR)

(72) Inventor: Wonseok Jang, Busan (KR)

( * ) Notice: Subject to any disclaimer, the term of this patent is extended or adjusted under 35 U.S.C. 154(b) by 0 days.

(21) Appl. No.: 15/759,510

(22) PCT Filed: Apr. 20, 2017

(86) PCT No.: PCT/KR2017/004241
§ 371 (c)(1),
(2) Date: Mar. 12, 2018

(87) PCT Pub. No.: WO2018/056544
PCT Pub. Date: Mar. 29, 2018

(65) Prior Publication Data
US 2019/0076194 A1 Mar. 14, 2019

(30) Foreign Application Priority Data

Sep. 22, 2016 (KR) .................. 10-2016-0121449

(51) Int. Cl.
*A61B 34/10* (2016.01)
*G06T 19/00* (2011.01)
*G06T 11/00* (2006.01)
*A61B 5/055* (2006.01)
*G06T 11/60* (2006.01)
(Continued)

(52) U.S. Cl.
CPC ............ *A61B 34/10* (2016.02); *A61B 5/0035* (2013.01); *A61B 5/0088* (2013.01); *A61B 5/055* (2013.01); *A61B 6/032* (2013.01); *A61B 34/25* (2016.02); *G06T 11/006* (2013.01); *G06T 11/60* (2013.01); *G06T 19/006* (2013.01); *A61B 2034/107* (2016.02); *G06T 2207/30036* (2013.01)

(58) Field of Classification Search
None
See application file for complete search history.

(56) References Cited

U.S. PATENT DOCUMENTS

| 2004/0029068 | A1* | 2/2004 | Sachdeva | A61C 7/00 433/24 |
| 2011/0153341 | A1* | 6/2011 | Diaz-Cortes | G16H 10/60 705/2 |
| 2015/0374460 | A1 | 12/2015 | Sachdeva et al. | |

FOREIGN PATENT DOCUMENTS

| JP | 2013-252428 A | 12/2013 |
| JP | 2016-016276 A | 2/2016 |

(Continued)

*Primary Examiner* — Yanna Wu
(74) *Attorney, Agent, or Firm* — Patent Office of Dr. Chung Park

(57) ABSTRACT

The present invention relates to an augmented reality system and implementation method for a dental surgery. In the augmented reality system and implementation method for a dental surgery of the present invention, an image convergence step, an interface step and an image projection step are performed. In the image convergence step, a common image obtained by photographing the face of a patient and a transmission image corresponding to the common image are collected, and the common image is mapped to the transmission image in a 3D image in which the common image and the transmission image overlap and registered with a server.

7 Claims, 5 Drawing Sheets

(51) Int. Cl.
*A61B 5/00* (2006.01)
*A61B 6/03* (2006.01)
*A61B 34/00* (2016.01)

(56) References Cited

FOREIGN PATENT DOCUMENTS

KR  10-2014-0015239 A  2/2014
KR  10-2015-0057030 A  5/2015

* cited by examiner

AUGMENTED REALITY SYSTEM AND METHOD FOR IMPLEMENTING AUGMENTED REALITY FOR DENTAL SURGERY

TECHNICAL FIELD

The present invention relates to a dental surgery using augmented reality and, more particularly, to an augmented reality system and implementation method for a dental surgery, wherein a 3D image corresponding to the face of a patient who undergoes a surgical operation is output to a user interface.

BACKGROUND ART

Dental surgeries, such as implant, a crown lengthening procedure and the extraction of a tooth, are performed by guessing the location of a bone based on a computed tomography (CT) image. Accordingly, the success or failure of the surgery may be determined by the ability of an operating surgeon, that is, the personal capability.

Recently, to prevent or minimize post-operational side effects, diagnosis and a treatment plan are established through the dental 3D CT images. With the help of the 3D CT images, a virtual surgery can be performed before the actual surgery. During the surgery, a surgical guide is used to further assist the surgeon, and to obtain better results.

Although the dental 3D images allowed a surgeon to have a virtual surgery, the success of the surgery is still strongly correlated with the clinical experience of the operating surgeon. Accordingly, the success rate of the surgery may be altered depending on the surgeon's capability.

Furthermore, an additional time and cost are wasted when a surgical guide is fabricated by a dental technical laboratory.

Therefore, a less technique-sensitive method is needed, that is, a surgical system based on highly accurate data, so a less experienced surgeon can still obtain improved surgical outcome.

In addition, there is an urgent need for the development of a new surgical operation method for reducing the cost and time required to fabricate a surgical guide by a dental technical laboratory.

DISCLOSURE

Technical Problem

An object of the present invention is to provide an augmented reality system and implementation method for a dental surgery, wherein a Common image (referring to the regular photo image obtained through a camera) and Transmission image (referring to the see-through image obtained by 3D CT images) corresponding to the face of a patient are collected and the collected images are mapped in a 3D image form and registered with a server so that the 3D image corresponding to the face of the patient who undergoes a surgical operation is output to a user interface.

Technical Solution

To achieve the technical object of implementing augmented reality for a dental surgery, the present invention performs an image convergence step and an interface step.

In the image convergence step, a plurality of common images of the face of a patient, the face and a plurality of transmission images corresponding to the face of a patient and to the common images are collected, the common images are mapped to the transmission images in a 3D image form in which the common images and the transmission images overlap, and the common images, transmission images and 3D images are registered with a server so that the images correspond to one another. In the interface step, a user terminal including a camera and a user interface and connected to the server is reflected in a different face, whether the reflected different face corresponds to the common image registered with the server is determined, and the 3D image is displayed in the user interface if the reflected different face corresponds to the common image.

Meanwhile, an augmented reality system for a dental surgery according to the present invention for achieving the technical object includes an image construction unit constructing a common image obtained by photographing the face of a patient, a transmission image corresponding to the common image, and a 3D image obtained by mapping the common image to the transmission image and an augmented reality processing unit outputting the common image, transmission image and 3D image or matching the common image, transmission image and 3D image to the face of the patient.

The image construction unit may include a common image photographing unit generating the common image by photographing the face of the patient; a transmission image photographing unit generating the at least one transmission image by transmitting and photographing the face of the patient corresponding to the common image; an image mapping unit mapping the common image to the transmission image in the 3D image form by overlapping the common image and the transmission image; and an image storage unit storing the common image, transmission image and 3D image.

The augmented reality processing unit may include a camera generating a facial image by photographing the face of a patient in real time; an authentication unit authenticating the patient by comparing the facial image with the common image; a user interface outputting the facial image, common image, transmission image and 3D image by matching the images to the face of the patient in real time when the authentication is completed; and a projection unit projecting the transmission image matched in real time onto the face part of the patient.

Advantageous Effects

As described above, in the augmented reality system and implementation method for a dental surgery according to the present invention, a common image and transmission image of the face of a patient are mapped in a 3D image form so that they overlap and are registered with a server. Accordingly, when an operating surgeon performs a surgical operation on the patient, he or she can receive the 3D image corresponding to the face of the patient and perform the surgical operation based on accurate data.

Furthermore, in the augmented reality system and implementation method for a dental surgery according to the present invention, a transmission image overlaps the face of a patient who undergoes a surgical operation. Even an operating surgeon who has insufficient clinical experiences can reduce a surgical operation time and safely perform a surgical operation.

Furthermore, the augmented reality system and implementation method for a dental surgery according to the present invention can reduce a cost and time wasted for the fabrication of a tool that helps a dental surgery, such as a surgical guide.

BEST MODE FOR INVENTION

Exemplary embodiments of the present invention may be modified in various forms, and the scope of the present invention should not be construed as being limited to the following embodiments. The present embodiments of the present invention are provided to a person having ordinary knowledge in the art to more fully describe the present invention.

The present invention is described in detail by describing preferred embodiments of the present invention with reference to the accompanying drawings.

Figure 1:
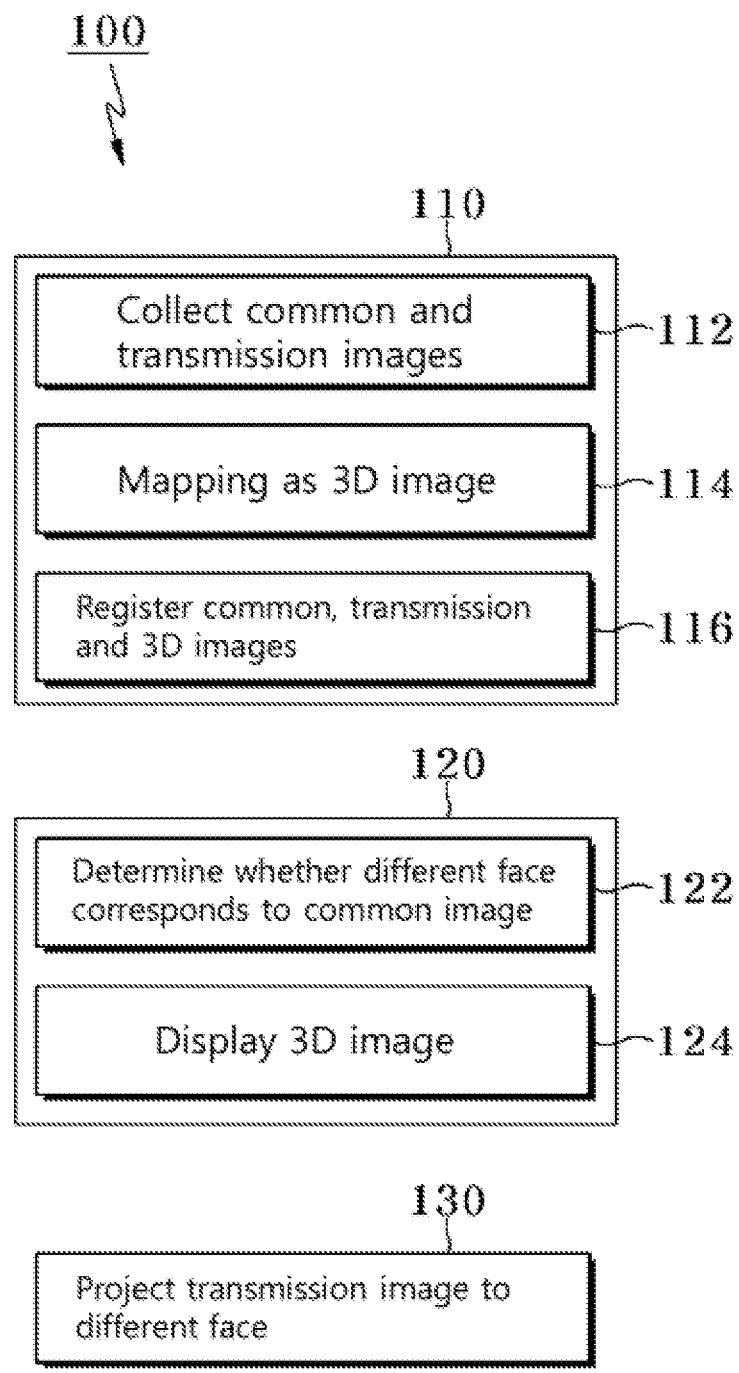
FIG. 1 shows a method of implementing augmented reality for a dental surgery according to the present invention.

FIG. 1 shows a method of implementing augmented reality for a dental surgery according to the present invention.

Although not shown in FIG. 1 in detail, the method 100 of implementing augmented reality for a dental surgery according to the present invention has been defined to include processes performed in a specific apparatus which controls the operations of an image collection unit, an image mapping unit and an image storage unit. When a processor performs the method 100 of implementing augmented reality for a dental surgery according to the present invention, the image mapping unit maps a common image and transmission image collected by the image collection unit so that they overlap in a 3D image form. A 3D image of a patient who undergoes a surgical operation is output to a user terminal and a transmission image is projected onto the face of the patient using the common image, the transmission image and the 3D image stored in the image storage unit. The image storage unit may be included in computer hardware for exchanging information, for example, a server. In this case, the transmission image is an image including at least one of an X-ray, CT and MRI and may be photographed through radiation photographing.

Referring to FIG. 1, in the method 100 of implementing augmented reality for a dental surgery, an image convergence step 110, an interface step 120 and an image projection step 130 are performed.

In the image convergence step 110, an image collection step 112, an image mapping step 114 and an image registration step 116 are performed.

In the image collection step 112, a common image and a transmission image are collected by photographing in a plurality of direction, that is, in multiple angles, so that the face of a patient, in particular, the mouth is well displayed. In the image collection step 112, a common image and a transmission image may be collected by photographing and using image information previously stored in a server.

In the image mapping step 114, the common image and the transmission image are mapped so that they correspond to each other in a 3D image form in a one-to-one or many-to-one manner and overlap it. In other words, what the common image and the transmission image correspond to each other in a one-to-one manner means that a single transmission image corresponds to a single common image. Furthermore, what the common image and the transmission image correspond to each other in a many-to-one manner means that a plurality of common images may correspond to a single transmission image. Furthermore, the common image and the transmission image corresponding to each other in a one-to-one or many-to-one manner overlap using an anatomical landmark, for example, retromolar pad, metal foramen or the border of the mandible as a reference point and are mapped in a 3D image form. Furthermore, in the 3D image, a nerve, such as nerve alveolaris inferior, may be identified using the anatomical landmark.

In the image registration step 116, the common image, the transmission image and the 3D image are registered with the server so that they correspond to one another. That is, the common image may be registered so that the transmission image corresponding to the common image and the 3D image corresponding to the common image are extracted from the common image. Furthermore, the transmission image may be registered so that the common image corresponding to the transmission image and the 3D image corresponding to the transmission image are extracted from the transmission image. Furthermore, the 3D image may be registered so that the common image corresponding to the 3D image and the transmission image corresponding to the 3D image are extracted from the 3D image.

This is summarized as follows. In the image convergence step 110, a plurality of common images corresponding to the face of a patient and a plurality of transmission images corresponding to the face and the common images are collected. The common images and the transmission images are mapped so that they overlap in a 3D image form. The common images, the transmission images and the 3D images are registered with a server in such a way as to correspond to one another. As described above, the server may be included so-called computer hardware and may exchange information with a user terminal and an imaging apparatus.

In the interface step 120, a face confirmation step 122 and a screen display step 124.

In the face confirmation step 122, a different face, for example, the face of a specific patient is reflected in the user terminal in order to determine whether the different face corresponds to a common image registered with the server. The different face means the face of a patient who is placed on an operating table and undergoes a surgical operation. In this case, whether the different face corresponds to the common image registered with the server may be determined by a facial recognition system, for example. If, as a result of the determination, the different face does not correspond to the common image registered with the server, in the face confirmation step 122, a surgical operation medical team, including an operating surgeon, and the patient may be warned that the different face does not correspond to the common image registered with the server. The reason for this is to prevent a surgical operation from being performed based on erroneous information because a 3D image corresponding to a common image registered with the server is extracted and thus if a 3D image of yet another face is extracted, another face of a patient placed on an operating table does not correspond to the 3D image of yet another face.

In the screen display step 124, if the different face corresponds to the common image registered with the server, a 3D image corresponding to the common image registered with the server is displayed in a user interface. The 3D image displayed in the user interface may be changed to correspond to a change in the different face of the patient placed on an operating table, for example, a change in various angles of the mouth structure of the different face. Regarding the various angles of the mouth structure of the different face, when the different face of a patient who undergoes a surgical operation, in particular, the mouth is further widened or closed, the mouth structure of the 3D image may be changed in response thereto.

This is summarized as follows. In the interface step 120, a different face is reflected in a user terminal including a camera and a user interface and connected to a server in order to determine whether the reflected different face corresponds to a common image registered with the server. If the different face corresponds to the common image, a corresponding 3D image is displayed in the user interface. Furthermore, in the interface step 120, if the reflected different face does not correspond to the common image registered with the server, a medical team and the patient who undergoes a surgical operation may be notified of the fact. The angle of the mouth of a corresponding 3D image may be changed, that is, adjusted in response to a change in various angles of the mouth structure of the patient who undergoes the surgical operation.

In the image projection step 130, a transmission image corresponding to the 3D image displayed in the screen display step 124 is transferred to a projection apparatus connected to the server, and is projected using the projection apparatus so that the transmission image overlaps the different face. The projection apparatus may include a beam projector, a laser projector or a video projector, for example. Furthermore, in the image projection step 130, when the transmission image is projected in such a way as to overlap the different face, it may be adjusted and projected in real time in response to a change in the angle of the mouth of the different face, that is, a mouth structure. In this case, the transmission image may include at least one of an X-ray, CT and MRI. As in the image mapping step 114, in the image projection step 130, when the angle of the mouth structure of the different face is changed, the transmission image projected onto the different face may be changed using an anatomical landmark, for example, retromolar pad, metal foramen or the border of the mandible as a reference point and may be matched with the different face.

Embodiments of the present invention to which a dental surgery using augmented reality may be applied are described with reference to FIGS. 2 to 4. The following embodiments are described with reference to the steps of FIG. 1.

Figure 2:
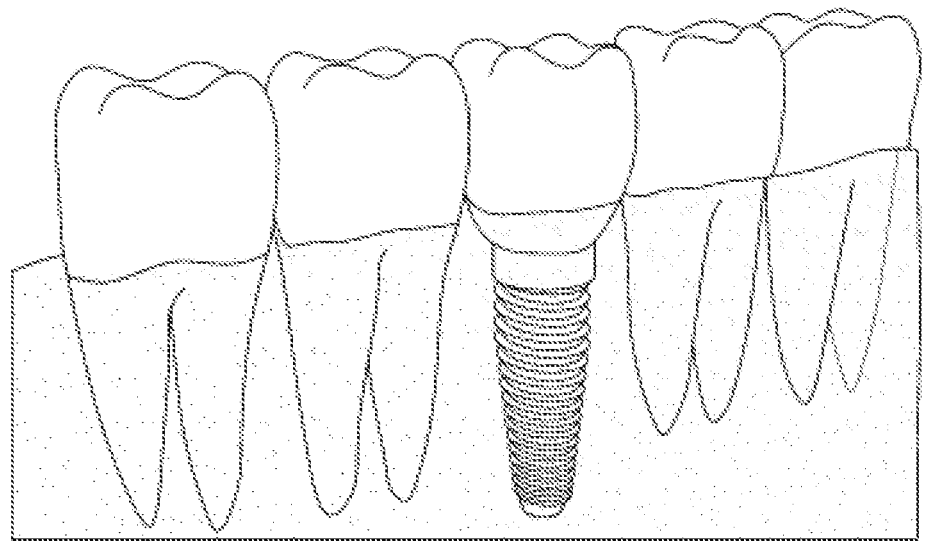
FIG. 2 shows the teeth structure of implant to which the method of implementing augmented reality for a dental surgery according to the present invention is applied.

FIG. 2 shows the teeth structure of implant to which the method of implementing augmented reality for a dental surgery according to the present invention is applied.

An implant means a fixture implanted within or on a jawbone in order to support a prosthetic appliance for the recovery of a missing tooth. In order to insert such implant into an accurate location, in the screen display step 124, a 3D image may be displayed in the user interface so that it is matched with the widening or narrowing of the face of a patient who undergoes a surgical operation, in particular, the mouth. In addition, in the image projection step 130, a transmission image may be projected using the projection apparatus so that it overlaps the face of a patient who undergoes a surgical operation. Accordingly, in the method 100 of implementing augmented reality for a dental surgery according to the present invention, a 3D image can be displayed in the user interface, and a transmission image can also be projected in such a way as to overlap the face of a patient who undergoes a surgical operation. Accordingly, an operating surgeon can confirm the location and angle of implant to be inserted into the gum of the patient.

Figure 3:
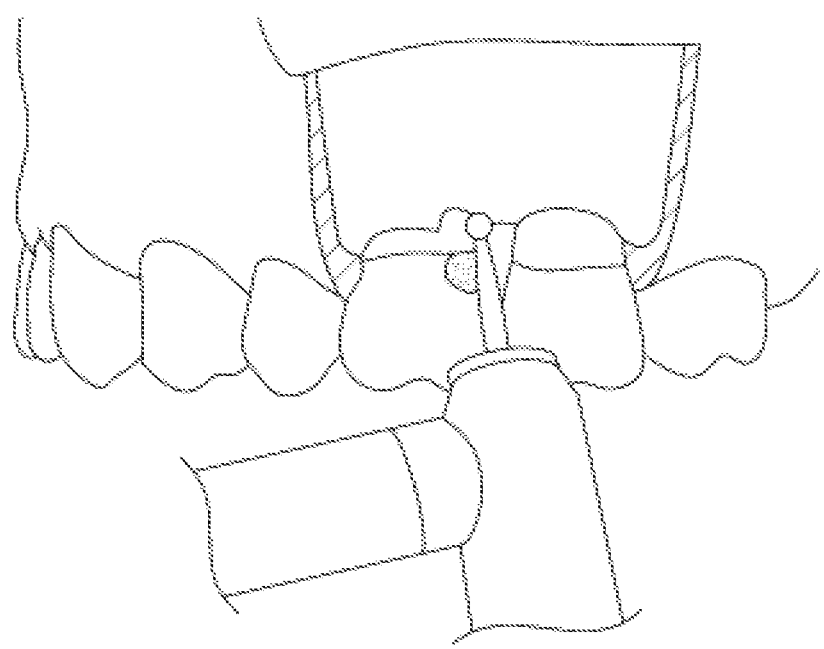
FIG. 3 shows the teeth structure of a crown lengthening procedure to which the method of implementing augmented reality for a dental surgery according to the present invention is applied.

FIG. 3 shows the teeth structure of a crown lengthening procedure to which the method of implementing augmented reality for a dental surgery according to the present invention is applied.

The crown lengthening procedure is a treatment method for increasing the height of a tooth by exposing a tooth portion covered with the gum. In order to facilitate the crown lengthening procedure, in the screen display step 124, a 3D image may be displayed in the user interface so that it is matched with the widening or narrowing of the face of a patient who undergoes a surgical operation, in particular, the mouth. In addition, in the image projection step 130, a transmission image may be projected using the projection apparatus so that it overlaps the face of a patient who undergoes a surgical operation. Accordingly, in the method 100 of implementing augmented reality for a dental surgery according to the present invention, a 3D image can be displayed in the user interface and a transmission image can also be projected in such a way as to overlap the face of a patient who undergoes a surgical operation, thereby enabling an operating surgeon to confirm an accurate length of a crown.

Figure 4:
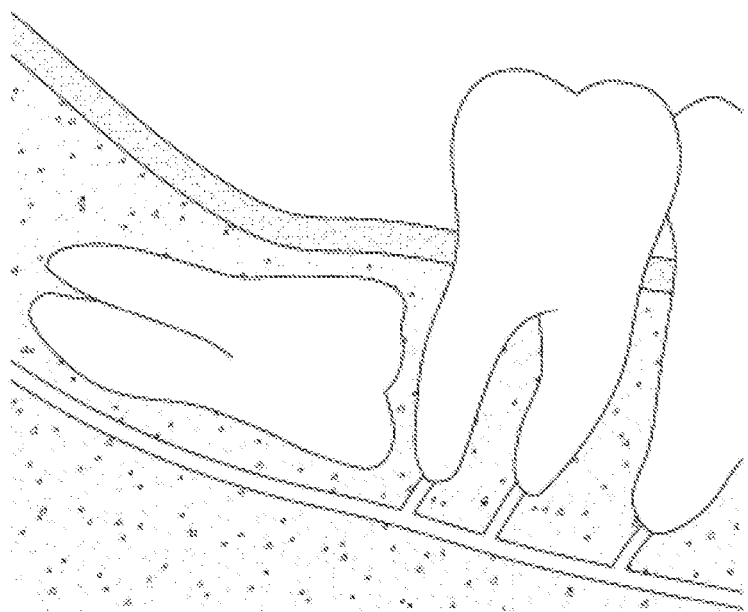
FIG. 4 shows a tooth extraction teeth structure to which the method of implementing augmented reality for a dental surgery according to the present invention is applied.

FIG. 4 shows a tooth extraction teeth structure to which the method of implementing augmented reality for a dental surgery according to the present invention is applied.

The extraction of a tooth, in particular, a wisdom tooth may give damage to an important anatomical structure, such as a nerve or the blood vessel of the gum. In the screen display step 124, a 3D image may be displayed in the user interface so that it is matched with the widening or narrowing of the face of a patient who undergoes a surgical operation, in particular, the mouth. In addition, in the image projection step 130, a transmission image may be projected using the projection apparatus so that it overlaps the face of a patient who undergoes a surgical operation. Accordingly, in the method 100 of implementing augmented reality for a dental surgery according to the present invention, a 3D image can be displayed in the user interface. Furthermore, in the method 100 of implementing augmented reality for a dental surgery, a transmission image can be projected so that it overlaps the face of a patient who undergoes a surgical operation. Accordingly, an operating surgeon can check where a tooth to be extracted is located in an important anatomical structure, for example, in a mouth structure.

MODE FOR INVENTION

An augmented reality system 200 for a dental surgery for executing the method of implementing augmented reality for a dental surgery according to the present invention is described below.

Figure 5:
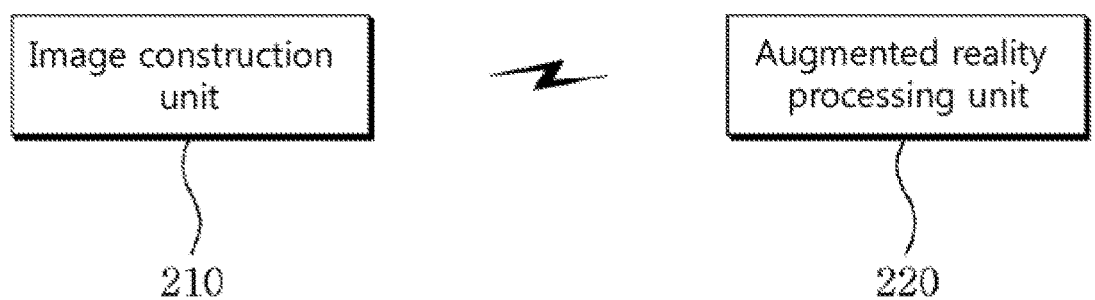
FIG. 5 is a block diagram of an augmented reality system 200 for a dental surgery according to an embodiment of the present invention.

FIG. 5 is a block diagram of an augmented reality system 200 for a dental surgery according to an embodiment of the present invention.

The augmented reality system 200 for a dental surgery according to the present invention includes an image construction unit 210 constructing a common image of the face of a patient, a transmission image corresponding to the common image and a 3D image obtained by mapping the common image to the transmission image and an augmented reality processing unit 220 (user terminal) outputting the common image, the transmission image and the 3D image or mapping it to the face of a patient.

In the augmented reality system 200 for a dental surgery according to the present invention, when the image construction unit 210 constructs a common image, transmission image and 3D image for the face of a patient using image equipment, the augmented reality processing unit 220 performs authentication by comparing an image obtained by capturing the face of a patient in real time with the images constructed in the image construction unit 210, selectively outputs the common image, transmission image and 3D image, and selectively projects the common image, transmission image and 3D image for the face of the patient. In this case, the 3D image is output to the user interface, and the transmission image is output to the face of the patient.

Meanwhile, the image construction unit 210 and the augmented reality processing unit 220 may be integrated and may be connected through wired/wireless communication. If the image construction unit 210 and the augmented reality processing unit 220 are connected through wired/wireless communication, a communication unit (not shown) is formed in each of the image construction unit 210 and the augmented reality processing unit 220. The image construction unit 210 and the augmented reality processing unit 220 perform synchronization, authentication processing and processing, such as image data transmission, through the corresponding communication units.

Figure 6:
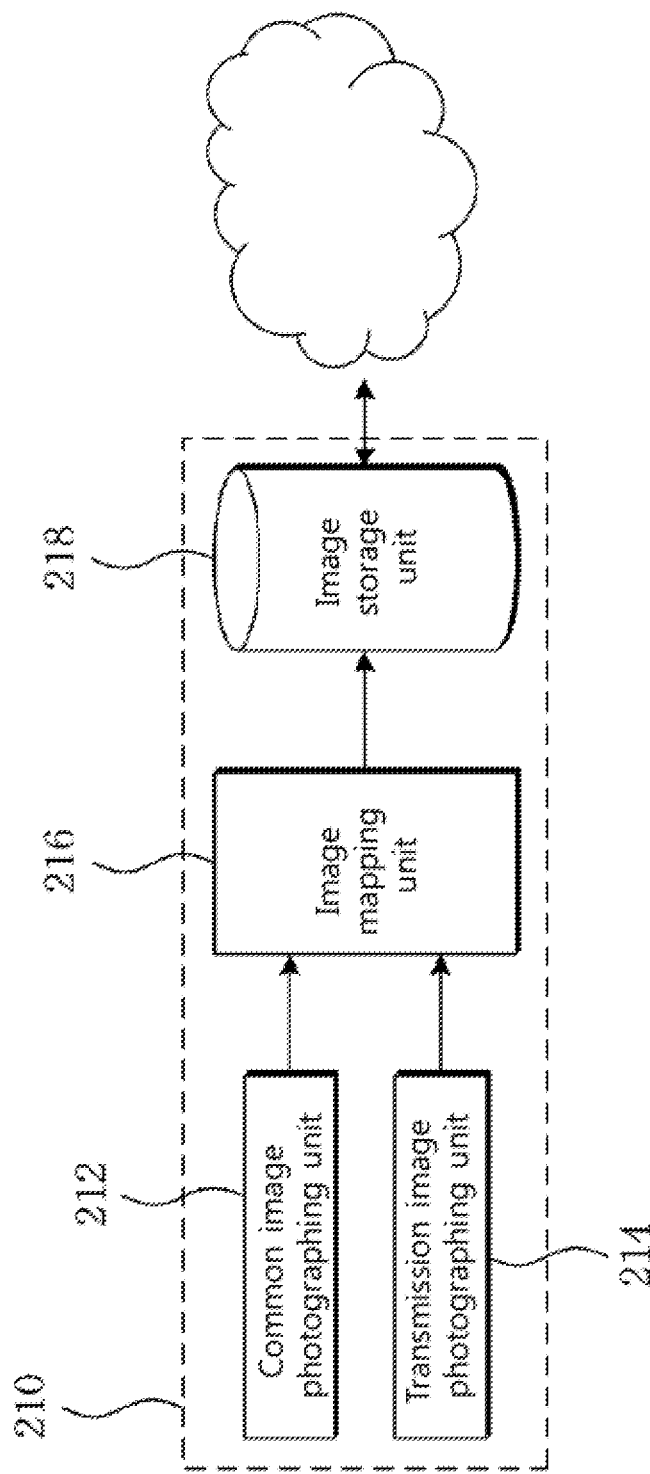
FIG. 6 is a block diagram of an image construction unit according to an embodiment of the present invention.

FIG. 6 is a block diagram of the image construction unit according to an embodiment of the present invention.

The image construction unit 210 of the present invention includes a common image photographing unit 212 generating a common image by photographing the face of a patient, a transmission image photographing unit 214 generating at least one transmission image by transmitting and photographing the face of the patient corresponding to the common image, an image mapping unit 216 mapping the common image to the transmission image so that they overlap in a 3D image form, and an image storage unit 218 storing the common image, transmission image and 3D image.

In this case, the common image photographing unit 212 and the transmission image photographing unit 214 may be configured to be capable of simultaneous photographing. Meanwhile, the common image photographing unit 212, the transmission image photographing unit 214, the image mapping unit 216 and the image storage unit 218 may be integrated to form a system and may be selectively combined to form a system.

Meanwhile, in the present embodiment, only the photographing of the face of a patient has been disclosed, but the inside of the mouth of a patient may be photographed and a transmission image and 3D image corresponding to the photographed image are constructed.

The image construction unit 210 of the present invention is controlled by a corresponding processor. The image mapping unit 216 generates a 3D image by overlapping images using retromolar pad, metal foramen or the border of the mandible, for example, as a reference point under the control of the corresponding processor. That is, the image mapping unit 216 generates a 3D image by overlapping images based on an anatomical important landmark. In this case, the anatomical landmark that is a basis means a landmark that distinctly appears in both a common image and a transmission image and whose shape or size is not frequently changed.

Figure 7:
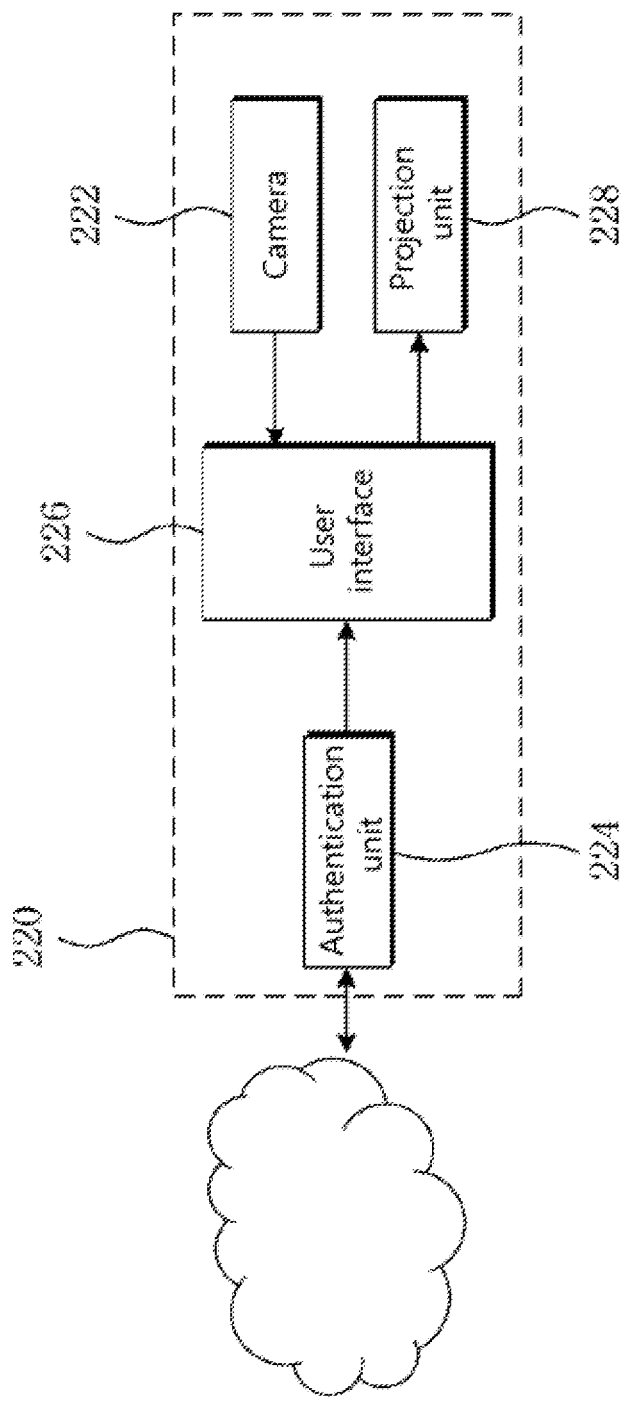
FIG. 7 is a block diagram of an augmented reality processing unit according to an embodiment of the present invention.

FIG. 7 is a block diagram of the augmented reality processing unit according to an embodiment of the present invention.

The augmented reality processing unit 220 of the present invention includes a camera 222 generating a facial image by photographing the face of a patient in real time, an authentication unit 224 authenticating the patient by comparing the facial image with a common image stored in the image storage unit 218, a user interface 226 matching the facial image, common image, transmission image and 3D image with the face of the patient in real time when the authentication is completed and outputting an image, and a projection unit 228 projecting a transmission image matched in real time onto the face part of the patient.

In this case, the authentication unit 224 may perform the authentication using a face recognition algorithm. Furthermore, a beam projector, a laser projector or a video projector may be used as the projection unit 228. Furthermore, the user interface 226 may perform a task for matching a facial image with other images (common image, transmission image and 3D image) in real time in addition to image output.

Meanwhile, the augmented reality processing unit 220 may be associated with a virtual reality (VR) device or all of corresponding elements may be installed on a VR device.

The image construction unit 210 of the present invention constructed as described above is controlled by a corresponding processor. The camera 222 generates an image of the face of a patient in real time under the control of the corresponding processor. The user interface 226 displays the facial image generated in real time and other images (common image, transmission image and 3D image) by matching the facial image with other images. The transmission image matched in real time is projected onto the mouth of the patient through the projection unit 228. The same image is output to the user interface 226 in response to a movement of the patient and may be projected onto the face of the patient.

As described above, as an image is directly projected onto the face of a patient, for example, the place where an implant is to be performed is displayed in real time, and the image is projected so that the inclination of the implant is guided or a nerve, a blood vessel, etc. that is not directly seen by the eye, but must be careful when a tooth is extracted is projected in real time. Accordingly, a doctor who has a low skill level can identify an accurate location when performing a surgical operation. Furthermore, a surgical operation success probability can be further improved because a surgical operation is performed while checking a 3D image output through the user interface 226.

The invention claimed is:

1. A method of implementing augmented reality for a dental surgery, comprising:
   an image convergence step of collecting a plurality of common images of a face of a patient and a plurality of transmission images corresponding to the plurality of common images, mapping the plurality of common images to the plurality of transmission images to construct a 3D image in which the plurality of common images and the plurality of transmission images overlap with one another, and registering the plurality of common images, the plurality of transmission images and the 3D image with a server so that the plurality of common images, the plurality of transmission images and the 3D image correspond to one another;

an interface step of capturing a common image of a different face by using of a user terminal comprising a camera and a user interface and connected to the server, determining whether the different face corresponds to a common image registered with the server, and displaying a 3D image corresponding to the common image registered with the server on the user interface if the different face corresponds to the common image registered with the server; and an image projection step of transferring a transmission image corresponding to the 3D image displayed at the interface step to a projection apparatus connected to the server and projecting the transmission image using the projection apparatus so that the transmission image overlaps the different face in real time, wherein the different face is a face of a patient to be treated, and when the transmission image is projected onto the different face in such a way as to overlap the different face in real time, the transmission image is adjusted and projected in real time in such a way as to be matched with the different face as an angle of a mouth of the different face is changed.

2. The method of claim 1, wherein the image convergence step comprises:

an image collection step of collecting the plurality of common images and the plurality of transmission images by capturing the plurality of common and transmission images at a plurality of angles;

an image mapping step of mapping the plurality of common images to the plurality of transmission images to construct the 3D image so that the plurality of common and transmission images correspond to one another in a one-to-one or many-to-one manner and overlap with one another; and an image registration step of registering the plurality of common images, the plurality of transmission images and the 3D image to the server so that the plurality of common images, the plurality of transmission images and the 3D image correspond to one another.

3. The method of claim 1, wherein the interface step comprises:

a face confirmation step of determining whether the different face corresponds to the common image registered with the server by using of the captured common image of the different face; and a screen display step of displaying the 3D image corresponding to the common image registered with the server on the user interface when the different face corresponds to the common image registered with the server.

4. The method of claim 1, wherein the plurality of transmission images include at least one of an X-ray, CT and MRI.

5. An augmented reality system for a dental surgery, comprising:

an image construction unit constructing a plurality of common images obtained by photographing a face of a first patient, a plurality of transmission images corresponding to the plurality of common images, and a 3D image obtained by mapping the plurality of common images to the plurality of transmission images; and an augmented reality processing unit outputting the plurality of common images, the plurality of transmission images and the 3D image or matching the plurality of common images, the plurality of transmission images and the 3D image to the face of the first patient, wherein the image construction unit performs:

an image convergence step of collecting the plurality of common images and the plurality of transmission images and the 3D image and registering the plurality of common images, the plurality of transmission images and the 3D image with a server so that the plurality of common images, the plurality of transmission images and the 3D image correspond to one other, wherein the augmented reality processing unit performs:

an interface step of capturing a common image of a different face, determining whether the different face corresponds to a common image registered with the server, and displaying a 3D image corresponds to the common image registered with the server on the user interface if the different face corresponds to the common image registered with the server; and an image projection step of transferring a transmission image corresponding to the 3D image displayed at the interface step to a projection apparatus connected to the server and projecting the transmission image using the projection apparatus so that the transmission image overlaps the different face in real time, wherein the different face is a face of a second patient to be treated, and when the transmission image is projected onto the different face in such a way as to overlap the different face in real time, the transmission image is adjusted and projected in real time in such a way as to be matched with the different face as an angle of a mouth of the different face is changed.

6. The augmented reality system of claim 5, wherein the image construction unit comprises:

a common image photographing unit generating the plurality of common images by photographing the face of the first patient;

a transmission image photographing unit generating the plurality of transmission images by transmitting and photographing the face of the first patient corresponding to the plurality of common images;

an image mapping unit mapping the plurality of common images to the plurality of transmission images to construct the 3D image by overlapping the plurality of common images with the plurality of transmission images; and an image storage unit storing the plurality of common images, the plurality of transmission images and the 3D image.

7. The augmented reality system of claim 5, wherein the augmented reality processing unit comprises:

a camera generating a facial image by photographing the different face in real time;

an authentication unit authenticating the different face by comparing the facial image with the plurality of common images;

a user interface outputting the facial image, common image corresponding to the facial image, a transmission image corresponding to the facial image and a 3D image corresponding to the facial image in real time when the authentication is completed; and the projection apparatus projecting the transmission image corresponding to the facial image in real time onto the face of the second patient.

* * * * *